United States Patent [19]

McGrail et al.

[11] Patent Number: 5,425,358

[45] Date of Patent: Jun. 20, 1995

[54] PRESSURE LIMITING VALVE FOR VENTILATION GAS APPARATUS

[75] Inventors: Thomas W. McGrail, Sparta; Ralph J. De Vito, Stanhope; James M. Howard, Dover, all of N.J.

[73] Assignee: Vital Signs, Inc., Totowa, N.J.

[21] Appl. No.: 178,525

[22] Filed: Jan. 6, 1994

Related U.S. Application Data

[62] Division of Ser. No. 923,468, Aug. 3, 1992, Pat. No. 5,301,667.

[51] Int. Cl.⁶ .................... A61M 16/00; A62B 7/00; A62B 9/02
[52] U.S. Cl. ............................ 128/205.24; 128/204.18
[58] Field of Search ............... 128/205.24, 202.27, 128/201.28, 204.26, 204.18; 207.12

[56] References Cited

U.S. PATENT DOCUMENTS

| | | | |
|---|---|---|---|
| 1,005,816 | 10/1911 | Drager | 128/202.27 |
| 2,406,888 | 9/1946 | Meidenbauer, Jr. | 128/202.27 |
| 4,077,404 | 3/1978 | Elam | 128/205.24 |
| 4,502,481 | 3/1985 | Christian | 128/205.24 |
| 5,109,840 | 5/1992 | Daleiden | 128/205.13 |
| 5,301,667 | 4/1994 | McGrail et al. | 128/205.24 |

FOREIGN PATENT DOCUMENTS

| | | | |
|---|---|---|---|
| 843576 | 3/1939 | France | 128/205.24 |
| 2137788 | 12/1972 | France | 128/202.27 |

*Primary Examiner*—Kimberly L. Asher
*Attorney, Agent, or Firm*—R. Gale Rhodes, Jr.

[57] ABSTRACT

Pressure limiting valve for being inserted into ventilation gas apparatus which valve includes a first vent for venting ventilation gas present in the apparatus above a first pressure to provide pressurized ventilation gas delivered to a person with a peak inspiratory pressure during periods of inspiration substantially equal to the first pressure, and including a second vent for venting accumulating pressurized ventilation gas present in the apparatus from increasing above a second pressure less than the first pressure to establish a base line pressure for the pressurized breathing gas to which the person is exposed during periods between periods of inspiration.

1 Claim, 3 Drawing Sheets

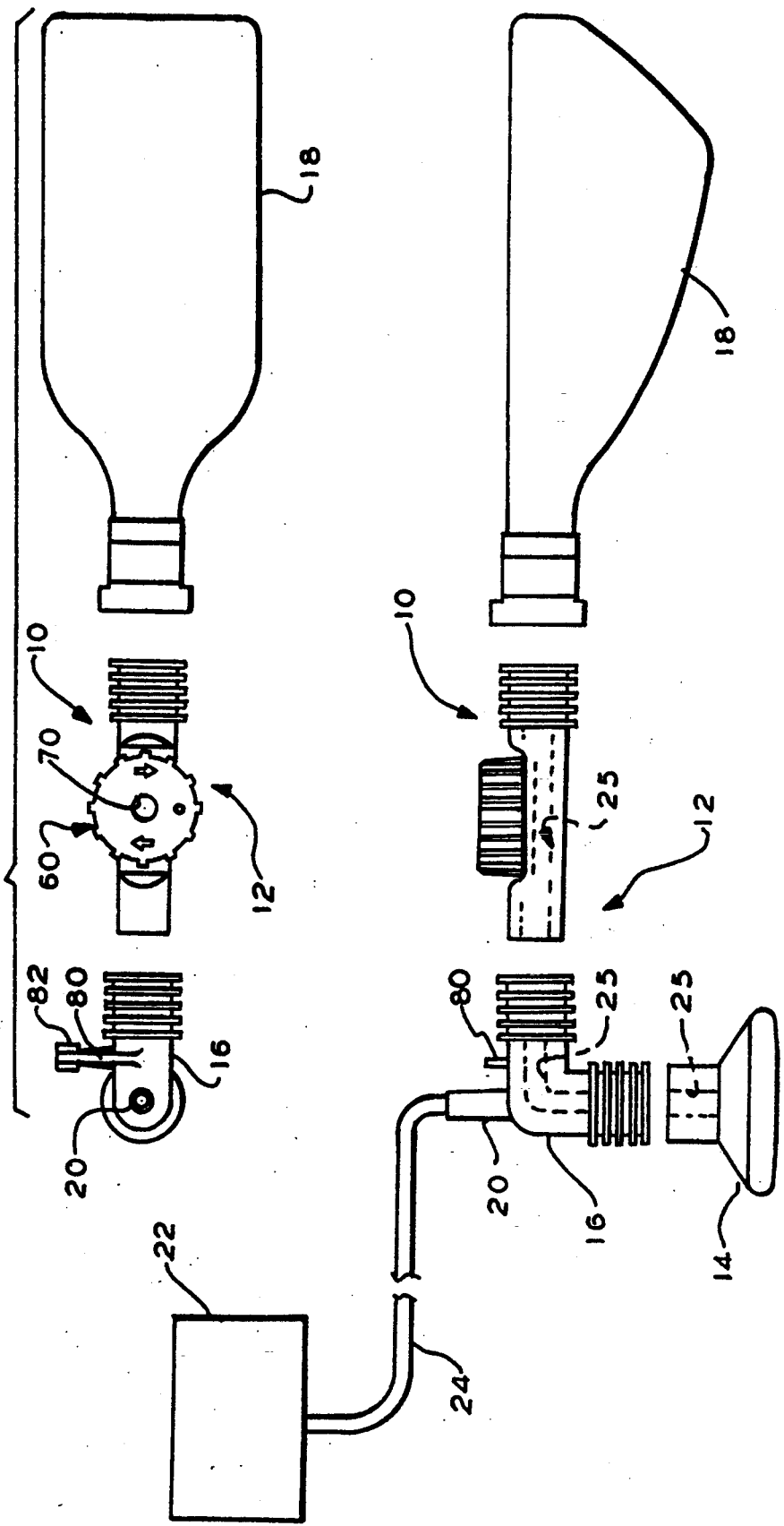

PRESSURE LIMITING VALVE FOR VENTILATION GAS APPARATUS

This is a division of application Ser. No. 07/923,468, filed Aug. 3, 1992, now U.S. Pat. No. 5,301,667.

BACKGROUND OF THE INVENTION

This invention relates generally to a new and improved pressure limiting valve for ventilation gas apparatus. More particularly, this invention relates to a new and improved adjustable pressure limiting valve for adjustably controlling the peak inspiratory pressure of ventilation gas with which a person, particularly an infant, is ventilated. Still more particularly, this invention relates to a new and improved pressure limiting valve for both adjustably controlling such peak inspiratory pressure and for providing a base line pressure for pressurized ventilation gas received by the apparatus from a source, and to which the person, particularly an infant, is exposed during periods between periods of inspiration.

As known to those skilled in the art, manual ventilation of infants with a ventilation gas such as compressed or pressurized oxygen is commonly indicated for resuscitation, for transport of ventilator-dependent infants, to increase the concentration of delivered ventilation gas and to oxygenate the infants prior to and after performing tracheobronchial suctioning.

A variety of reusable and disposable devices comprising ventilation gas apparatus are known to the art for manual ventilation of a person such as an infant. These apparatus can generally be categorized into two types: self-inflating or flow-dependent breathing bag apparatus. Regardless of the type, the primary problem or objective in ventilating infants is to control the pressure of the ventilation gas delivered to the infants. Infants are particularly challenging in this regard in that their lungs are more fragile than those of adults but less compliant, therefore, fine control of delivered peak inspiratory pressure of the ventilation gas delivered to an infant is critical. Furthermore, base line pressure, i.e. the pressure of the ventilation gas present in the ventilation gas apparatus and to which the lungs of the person being ventilated are exposed during periods between the periods the ventilation gas is delivered to the patient, i.e. periods between delivered breaths, must be controlled to prevent collapse or over-distension of the person's lungs, particularly those of an infant. Control of such base line pressure is particularly important for infants being ventilated because such control, it is believed, at least facilitates exhalation by the infant during the periods between the periods the infant is being ventilated or the periods between delivered breaths.

Numerous relatively complicated pressure limiting valves, and pressure limiting valve systems, are known to the art for controlling the peak inspiratory pressure of ventilation gas delivered to a person such as an infant during manual ventilation. In most instances, however, the delivered peak inspiratory pressure of the ventilation gas by such prior art apparatus is largely dependent on operator technique in compressing or squeezing the breathing bag which, upon squeezing or compression, delivers the ventilation gas to the person through the ventilation gas apparatus. The self-inflating breathing bag ventilation apparatus known to the art typically include a fixed pop-off valve as a safety back-up to prevent delivery to the infant of undesirably high or elevated inspiratory ventilation gas pressures, but such known valves and valve systems typically are not adjustable whereby the pressure of the delivered ventilation gas up to the level of the pop-off pressure of the fixed pop-off valve remains dependent upon the technique of the operator compressing the self-inflating breathing bag. Ventilation gas apparatus employing flow-dependent breathing bags typically incorporate a simple adjustable bleed valve having an adjustable orifice to control the exhaust pressure of the ventilating gas. This bleed valve has been found to be effective only to obtain an acceptable base line pressure at the flow rate of the ventilation gas into the ventilation gas apparatus. However, this type of ventilation gas apparatus is very flow-dependent whereby a small difference in operator technique of squeezing or depressing the flow-dependent breathing bag can significantly alter the delivered inspiratory pressure of the ventilation gas.

Also known to the art are reusable, adjustable metal pop-off valves which incorporate a spring and disc and which are also known for controlling the peak inspiratory pressure of ventilating gas delivered to a person such as an infant during ventilation, e.g. during resuscitation. These pop-off valves, which are generally known in the art as adjustable pressure limiting valves, apparently are at present the most effective in limiting the peak inspiratory pressure of ventilation gas delivered to infants. However, because these pop-off valves only relieve pressure once the preset threshold is attained, an undesirable build-up of the ventilation gas in the apparatus, to which the person being exposed or subjected, is possible during periods between periods during which the person is being ventilated with the ventilation gas or during periods between delivered breaths. This condition is sometimes referred to in the art as elevated base line pressure or inadvertent PEEP (Positive End Expiratory Pressure). If such base line pressure becomes too high, particularly during the periods between the periods the infant is being ventilated, it is believed that the ability of the infant to exhale can be greatly impaired. Furthermore, these valves suffer from the disadvantages of other reusable devices in that they are expensive, they must be disassembled for cleaning between use and thereafter reassembled, and they must be periodically maintained.

Accordingly, there exists a need in the art for a new and improved pressure limiting valve for insertion into ventilation gas apparatus which can be mechanically or manually adjusted to provide control, particularly adjustable control, of the peak inspiratory pressure of the ventilation gas substantially independent of operator technique in compressing or squeezing the breathing bag. Further, there exists a need in the art for a new and improved adjustable pressure limiting valve for insertion into ventilation gas apparatus which provides or limits a base line pressure for the ventilation gas also substantially independent of the technique of the operator in squeezing or compressing the breathing bag. Still further there exists a need in the art for a new and improved adjustable pressure limiting valve which provides control of both such peak inspiratory ventilation gas pressure and such base line pressure.

SUMMARY OF THE INVENTION

The object of the present invention is to satisfy the foregoing needs in the ventilation gas apparatus art. A pressure limiting valve satisfying the foregoing needs and embodying the present invention may include a first vent for limiting the pressure of the ventilation gas present in the ventilation apparatus upon the compression of a breathing bag whereby the peak inspiratory pressure of the ventilation gas delivered to a person, such as an infant, is limited or controlled, and which valve may further include a second vent for limiting the base line pressure of the pressurized ventilation gas to which the person, particularly an infant, is exposed during periods between the periods of delivery of the pressurized ventilation gas to such person or periods between the delivered breaths.

DESCRIPTION OF THE DRAWINGS

FIG. 1 is an exploded elevational side view of a ventilation gas apparatus into which the new and improved pressure limiting valve of the present invention may be inserted;

FIG. 2 is a top view of a portion of the ventilation gas apparatus of FIG. 1;

DESCRIPTION OF THE PREFERRED EMBODIMENT

Figure 5:
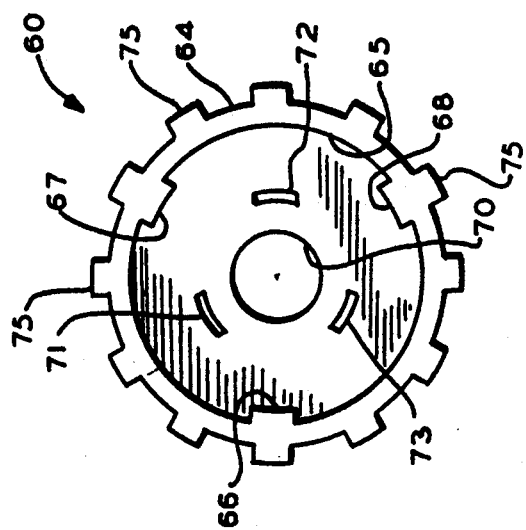
FIG. 5 is a bottom view of the cap shown in FIG. 3.

Referring to FIGS. 1 and 2, a pressure limiting valve embodying the present invention is identified by general numerical designation 10 and is shown, in exploded form, for insertion into a ventilation gas apparatus indicated by general numerical designation 12. Ventilation gas apparatus 12 may include a face mask 14, an elbow 16, the pressure limiting valve 10, and a flow-dependent breathing bag 18. The elbow 16, as shown in FIG. 1, may be provided with a connector 20 for connecting the ventilation gas apparatus 12 to a source of flow-regulated pressurized ventilation gas 22 which is typically found, for example, in a hospital. The connector 20 may be connected to the source 22 by a suitable flexible hose 24. It will be understood that although the components of the ventilation gas apparatus 12 shown in FIGS. 1 and 2 are shown in separate or exploded form, the components are typically interconnected by suitable hoses, such as flexible hoses, known to the art or other known interconnecting means. Upon interconnection of the components a ventilation gas flow passageway 25, indicated by the interrupted dashed lines in FIG. 1, is established between the breathing bag 18 and the face mask 14. It will be generally understood, and as known to those skilled in the art, that in operation the face mask 14 is placed over the mouth and nose of a person to be ventilated, e.g. an infant, and the operator alternately squeezes or compresses the bag 18 and releases (or at least partially releases) the bag 18 to allow the bag to refill with pressurized ventilation gas. Upon such squeezing or compression of the bag 18, the pressurized ventilation gas received by the bag 18 from the source 22 over the passageway 25 is further pressurized by the bag and is delivered to the person through the passageway 25 for inspiration; thereafter the operator releases, or at least partially releases the bag, or allows the breathing bag 18 to refill with pressurized ventilation gas to allow the person being ventilated to exhale.

The periods during which the breathing bag 18 is being compressed and further pressurized breathing gas is being delivered to the person for inspiration are sometimes referred to as inhalation periods, and the periods between such periods when the breathing bag is allowed to at least partially expand and refill are sometimes referred to as exhalation periods.

As may be noted from FIGS. 1 and 2, the pressure limiting valve 10 may be inserted in the ventilation gas apparatus 12 intermediate the connector 20 and the breathing bag 18, or the valve 10 may be inserted in other positions in the ventilation gas apparatus 12, such as for example between the elbow 16 and the face mask 14. As known to those skilled in the ventilation gas apparatus art, delivery devices other than a face mask, such as face mask 14, are utilized with ventilation gas apparatus, such as for example an endotracheal tube.

An understanding of the structure of the preferred embodiment of the adjustable pressure limiting valve 10 embodying the present invention may be understood by reference to FIGS. 3-6. The valve 10 may include a valve body indicated by general numerical designation 30 which includes a first generally cylindrical portion or member 32 provided with a centrally formed ventilation gas communication passageway 33 extending longitudinally therethrough and for forming a portion of a ventilation gas flow passageway 25 of FIG. 1. Valve body 30 may further include a second generally cylindrical portion or member 34 formed integrally with and generally perpendicular to the first generally cylindrical member 32 and provided with a generally centrally formed exhaust passageway 36 extending longitudinally therethrough and in fluid communication with the communication passageway 33 through an interconnecting circular inlet opening 38 formed in the lower portion of the exhaust passageway 36 as particularly shown in FIG. 6. The second generally cylindrical member 34, FIGS. 3 and 6, includes or is provided with a generally annular valve seat 40 residing in the lower portion of the exhaust passageway 36 and generally surrounding the inlet opening 38. The second generally cylindrical member 34 may further include a plurality of radially disposed internal ribs extending inwardly into the exhaust passageway 36, only ribs 37a and 37b being shown in FIG. 6. The exterior of the second generally cylindrical member 34 is provided with a plurality of axially aligned spiral grooves 41, 42 and 43. It will be understood from FIG. 3 that the spiral grooves 41, 42 and 43 have a common angle of inclination.

It will be generally understood that the valve 10, FIGS. 3-6, may further include a generally circular disc indicated by general numerical designation 45, a compression spring indicated by general numerical designation 50, and a cap indicated by general numerical designation 60.

Figure 4:
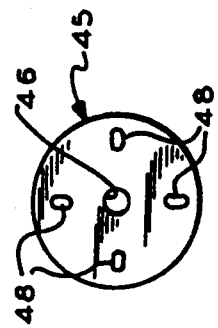
FIG. 4 is a top view of the disc shown in FIG. 3.
Figure 3:
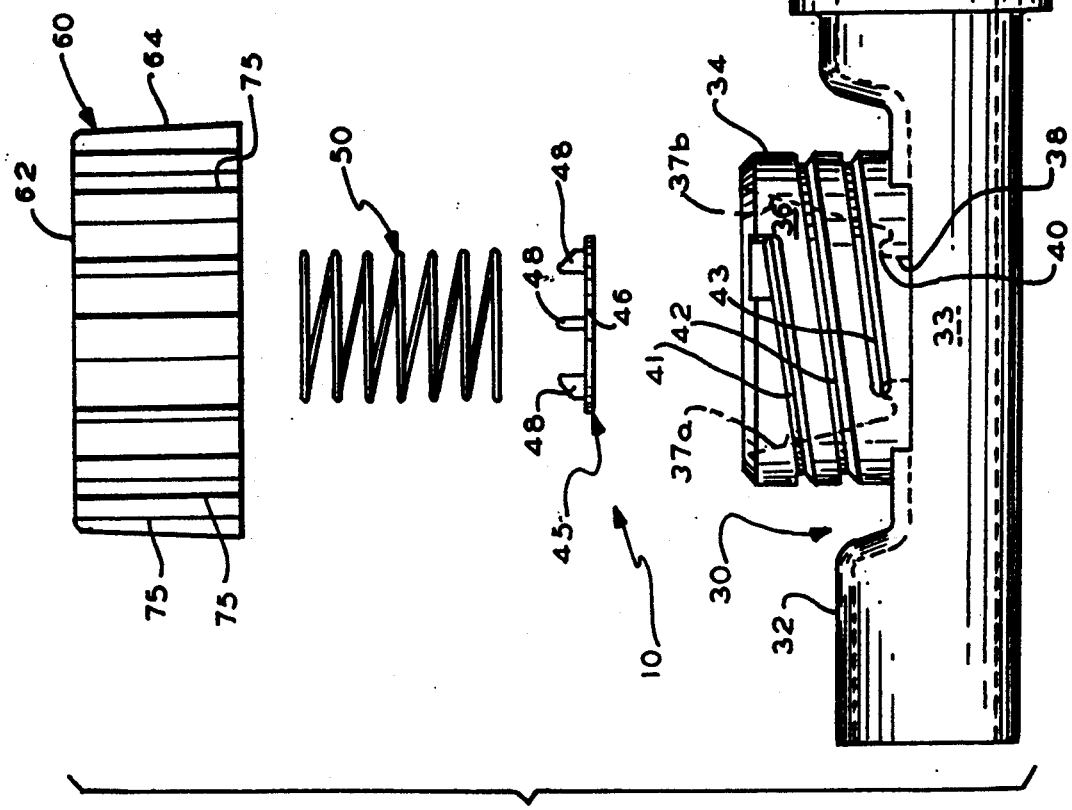
FIG. 3 is an exploded elevational side view of a preferred embodiment of an adjustable pressure limiting valve of the present invention.

The disc 45 may be provided with a generally centrally formed bleed hole or aperture 46, FIG. 4, and may be provided on one side, the top side as shown in FIGS. 3 and 4, with a plurality of outwardly or upwardly extending, spaced apart, members 48 generally surrounding the bleed hole 46.

Figure 6:
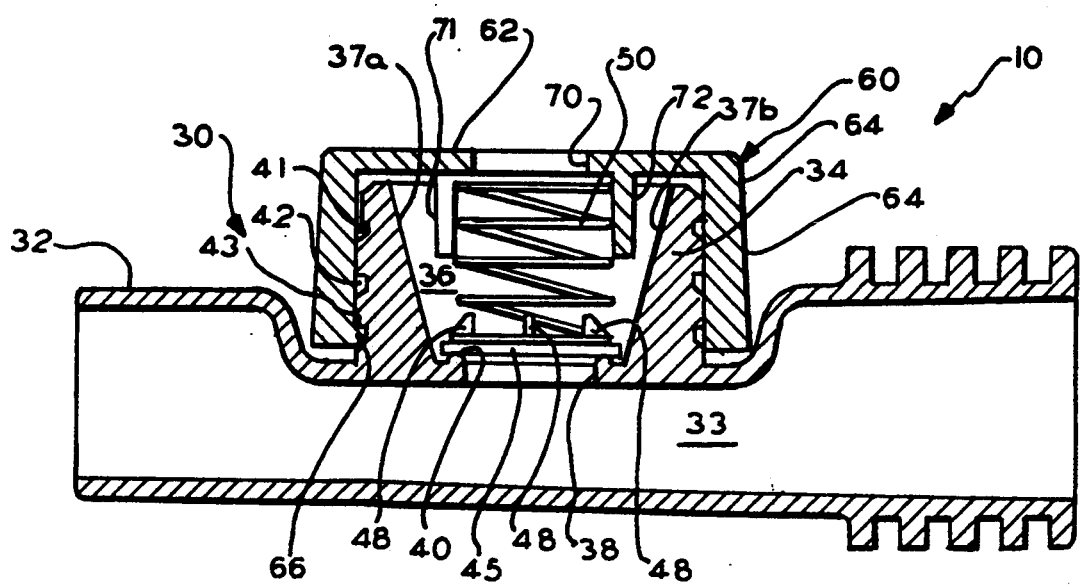
FIG. 6 is a side elevational view, in cross-section, of the adjustable pressure limiting valve of the present invention shown in FIGS. 1 and 3.

The cap 60, FIGS. 3, 5 and 6, may include a generally circular top 62 and a downwardly extending cylindrical wall 64 circumscribing the top 62 and oriented or disposed generally perpendicularly with respect to the top as may be better understood by reference to FIG. 6. As shown in FIG. 5, the interior 65 of the cap wall 64 may be provided with a plurality of inwardly extending groove engaging tabs 66, 67 and 68 equal in number to the plurality of spiral grooves 41, 42 and 43 provided on the exterior of the second generally cylindrical member 34 of the valve body 30, FIG. 3. It will be understood that the tabs 66, 67 and 68 are provided with substantially the same angle of inclination as the spiral grooves 41, 42 and 43 (FIG. 3) and it will be understood from FIG. 5 that adjacent groove engaging tabs are generally spaced circumferentially from each other by 120° and thus it will be understood that the groove engaging tabs 66, 67 and 68 are spaced substantially equally circumferentially with respect to each other around the interior of the cap wall 64. The cap 60, FIG. 5, may be provided with the generally centrally formed vent port 70 extending therethrough and may be further provided with a plurality of spaced apart generally arcuate members 71, 72 and 73 extending downwardly from the interior or underside of the cap top 62 and generally surrounding the vent port 70. To facilitate manual rotation of the cap 60 with respect to the second generally cylindrical member 34 of the valve body 30, FIG. 3, such rotation being described in detail below, the exterior of the cap wall 64 may be provided with a plurality of outwardly extending, spaced apart ribs 75 as may be best seen in FIGS. 3 and 5.

Upon assembly, the components of the valve 10 generally occupy the positions shown in FIG. 6, the members 48 extending upwardly from the disc 45 generally engage the lower end portion of the spring 50 and the arcuate members 71, 72 and 73 extending downwardly from the underside of the cap top 62 generally engage the upper end portion of the spring 50 and such opposed tabs generally maintain the spring 50 in general axial alignment with the inlet opening 38, the disc 45, the exhaust passageway 36, and the vent port 70 formed in the cap top 62; the inwardly extending ribs formed on the interior of the second generally cylindrical member 34, e.g. ribs 37a and 37b shown in FIG. 6, also assist maintaining the disc 45 generally in axial alignment with respect to the inlet opening 38, the exhaust passageway 36 and the vent port 70. During assembly, the cap 60 is moved or forced downwardly to cause the groove engaging tabs 66, 67 and 68 to initially snap into the top portions of the spiral grooves 41, 42 and 43 and cause each of such tabs to reside in one of the grooves; in FIG. 6 groove engaging tab 66 is shown residing in spiral groove 43. It will be generally understood that upon the groove engaging tabs 66, 67 and 68 residing in the spiral grooves 41, 42 and 43, the cap 60 is mounted rotatably with respect to the second generally cylindrical member 34 for both clockwise and counterclockwise directions of rotation with respect to the member 34. As will be understood by reference to FIG. 6, upon the cap 60 being rotated in the clockwise direction with respect to the second generally cylindrical member 34, the cap is screwed or moved increasingly downwardly over the member 34 causing the cap to increasingly compress the spring 50 and to cause the spring 50 to increase the force with which the disc 45 is forced into engagement with the valve seat 40. Upon the cap 60 being rotated in the counterclockwise direction with respect to the second generally cylindrical member 34, the cap is screwed or moved upwardly with respect to the member 34 causing the cap 50 to allow the spring to increasingly decompress to decrease the force with which the disc 45 is forced into engagement with the valve seat 40. Referring again to FIG. 6, it will be understood that upon such assembly and upon the spring 50 being compressed the disc 45 is forced into engagement with the valve seat 40 and the inlet opening 38 is closed, but that upon the disc 45 being forced upwardly out of engagement with the valve seat 40 in the manner described below, the communication passageway 33 formed in the cylindrical member 32, the inlet opening 38 and the exhaust passageway 36 formed in the second generally cylindrical member 34 and the vent port 70 formed in the cap top 62 are all in fluid communication.

In operation, it will be assumed that the components of the valve 10 have been assembled as shown in FIG. 6 and described above, that the valve 10 has been inserted into the ventilation gas apparatus 12 of FIGS. 1 and 2, that the components of the ventilation gas apparatus 12 have been assembled or interconnected as described above, that the connector 20 has been connected to the flow-regulated source of ventilation gas 22 through the hose 24 and that the face mask 14 has been placed over the face of a person such as an infant to be ventilated. It will be further assumed that the cap 60 has been manually rotated in either the clockwise or counterclockwise direction by the operator to determine or establish the force with which the disc 45, FIG. 6, is forced into engagement with the valve seat 40 by the spring 50. It will be generally understood, and as described in further detail below, that it is the establishment or determination of the force with which the disc 45 is forced into engagement with the valve seat 40 by the spring 50 that determines the peak inspiratory pressure at which the further pressurized ventilation gas is delivered from the breathing bag 18 to the infant upon compression of the breathing bag 18. Continuing with the description of operation, flow regulated pressurized ventilation gas from the source 22, FIG. 1 will flow into the breathing bag 18 through the hose 24, the connector 20, and a portion of the flow passageway 25 of the ventilation gas apparatus 12 which includes the ventilation gas communication passageway 33 (FIGS. 3 and 4) formed in valve 10. The operator will compress or squeeze the breathing bag 18 to cause the pressurized ventilation gas received therein to be further pressurized and to be delivered through the flow passageway 25, FIG. 1, extending through the valve 10, elbow 16, and mask 14 to the lungs of the infant to ventilate the infant with the ventilation gas.

As may be best understood by reference to FIG. 6, the disc 45, specifically the underside of the disc, is exposed to pressurized ventilation gas present in the passageway 33 and in particular is exposed to the further pressurized ventilation gas produced by the squeezing or compression of the breathing bag 18, FIGS. 1 and 2. The further pressurized ventilation gas present in the passageway 33, FIG. 6, will act against the underside of the disc 45 to produce a force acting in opposition to the force applied to the disc 45 by the compression spring 50. Upon the force applied to the disc by the further pressurized ventilation gas exceeding the force applied to the disc 45 by the spring 50, the spring 50 will further compress to cause the disc 45 to be moved out of engagement with the valve seat 40 whereby a portion of the further pressurized ventilation gas will be exhausted or vented through the inlet opening 38, the exhaust passageway 36, and the vent port 70 provided in the cap top 62 to vent or exhaust such further pressurized ventilation gas to the ambient or atmosphere. Such further pressurized gas will be exhausted or vented until the force applied to the underside of the disc 45 by the further pressurized ventilation gas acting thereagainst is less than the force applied to the top of the disc 45 by the compression spring 50 whereupon the disc will be returned to engagement with the valve seat 40 by the spring 50 and the further pressurized ventilation gas will no longer be vented or exhausted. Thus it will be understood that by rotating the cap 60 clockwise or counterclockwise with respect to the second generally cylindrical member 34 to establish the force with which the compression spring 50 forces the disc 45 into engagement with the valve seat 40, the peak inspiratory pressure of the further pressurized breathing gas delivered to the infant upon compression of the breathing bag 18 is established or determined manually or mechanically by the valve 10 and is substantially independent of the breathing bag squeezing or compressing technique of the operator. It will be further understood that between the extreme clockwise and counterclockwise rotational positions of the cap 60 with respect to the member 34, the force with which the disc 45 is forced into engagement with the valve seat 40 by the compression spring 50 may be varied substantially infinitely whereby the peak inspiratory pressure of the further pressurized ventilation gas can be varied substantially infinitely within such limits.

Referring now to the establishment of the base line pressure by the valve 10 of the present invention, the bleed hole 46 formed in the disc 45, FIG. 4, constantly vents a portion of the pressurized ventilation gas present in the ventilation gas communication passageway 33 of the valve 10, FIG. 6, to the ambient or atmosphere, specifically a portion of the pressurized ventilation gas present in the passageway 33 is constantly vented to the ambient or atmosphere through the inlet opening 38, the bleed hole 46, the exhaust passageway 36 and the exhaust port 70 formed in the cap top 62. It will be understood that the bleed hole 46 is sufficiently small to permit the further pressurized ventilation gas present in the passageway 33 to act against the underside of the disc 45 to produce the above-described force in excess of the force with which the disc is forced into engagement with the valve seat 40 by the compression spring 50. It will be further understood that during periods of exhalation by the infant, or during the periods between the periods where the breathing bag 18 is being compressed, the ventilation gas apparatus 12 is substantially closed due to the face mask 14 being in engagement with the face of the infant. Since the ventilation gas apparatus 12 is substantially closed, flow regulated pressurized ventilation gas from the source 22 will accumulate in the flow passageway 25 of the ventilation gas apparatus 12, FIG. 1, and the pressure of the accumulating ventilating gas in the flow passageway 25 will increase but will only increase to the predetermined base line pressure generally determined by the size of the bleed hole 46 which constantly vents a portion of the accumulating pressurized ventilating gas to the ambient or atmosphere, as described above, whereby the pressure of the accumulating pressurized ventilating gas does not exceed a pressure level determined generally by the size of the bleed hole 46. In one embodiment of the present invention the bleed hole 46 is approximately 2 mm in diameter to prevent an increase above an undesirable pressure level (base line pressure) due to the pressurized ventilation gas accumulating in the ventilation gas apparatus 12 at an influx rate from the flow regulated ventilation gas source at approximately 5-10 LPM. Thus, it will be understood that the bleed hole 46 is sufficiently large to establish the desired base line pressure. The sizing and principle behind the bleed hole 46 are similar to that employed in what the art or industry calls a non-rebreathing pressure relief elbow.

It will be noted that the valve 10 of the present invention is comprised of only four components, the valve body 30, disc 45, spring 50 and cap 60. The disc 45, cap 60 and body 30 may be inexpensively molded from a suitable plastic, such as by suitable injection molding, whereby the valve 10 of the present invention may be so inexpensive as to be disposable; molding from such plastic permits the cap 60 to be readily assembled to the valve body 30 by snap assembly of the groove engaging tabs 66, 67 and 68 and the spiral grooves 41, 42 and 43. The spring 50 may be inexpensively produced, in the manner known to those skilled in the art, from plastic or a variety of inexpensive metals, preferably a relatively inexpensive stainless steel.

It will be understood from FIG. 6 that the elements or components of the valve 10 providing the peak inspiratory pressure and the base line pressure are combination elements or components in that the elements or components providing the base line pressure are a portion of the elements or components providing the peak inspiratory pressure. More particularly, the elements or components providing the peak inspiratory pressure are the second generally cylindrical member 34 providing the exhaust passageway 36 and the inlet opening 38, the disc 45, the spring 50 and the cap top 62 providing the vent port 70, and the components or elements providing the base line pressure are the second generally cylindrical member 34 providing the inlet opening 38 and exhaust passageway 36, the disc 45 providing the bleed hole 46 and the cap top 62 providing the vent port 70.

Referring again to FIGS. 1 and 2 and FIG. 6, it will be understood that for brief periods of desired hyperinflation of a person's lungs, such as may be required to initially fill an infant's lungs at birth, the valve 10 may be temporarily overridden by closing or occluding the vent port 70 formed in the cap top 62 with the finger of the operator whereby elevated pressure levels may be achieved for the pressurized ventilation gas delivered to the infant's lungs upon compression of the breathing bag 18.

Referring again to FIGS. 1 and 2, it will be understood that the elbow 16 may be provided with a fitting or connector 80 including an internal passageway (not shown) in fluid communication with the flow passageway 25 (FIG. 1) of the ventilation gas apparatus 12 to permit the ventilation gas apparatus to be connected to a suitable monitor for monitoring the inspiration and exhalation periods in the manner known to those skilled in the art. Connector or fitting 80 may be provided with a suitable cap 82 (FIG. 2) for suitable closure if monitoring is not desired or required. Also, referring again to FIG. 6, it will be understood that by providing the second cylindrical member 34 with a plurality of axially aligned spiral grooves 41, 42 and 43 and by providing the interior cap wall 65 with a corresponding plurality of spiral groove engaging tabs 66, 67 and 68, the cap 60 may be mounted more stably, and prevented from rocking, with respect to the second generally cylindrical member 34, than would be the situation had only a single spiral groove and a single groove engaging tab been provided.

In the event that it is not desired to provide the above-noted base line pressure, the disc 45 will not be provided with the bleed hole 46 and the pressure limiting valve of the present invention will control the peak inspiratory pressure of the ventilation gas as described above.

As is further known to those skilled in the art, for spontaneously breathing patients, CPAP (Constant Positive Airway Pressure) is often employed to prevent collapse of alveoli and to reduce the work of breathing. The improved pressure limiting valve of the present invention, with or without the bleed hole 46 in the disc 45, can be incorporated into a manual resuscitation circuit or a CPAP circuit to allow CPAP to be adjusted to whatever level is desired. As opposed to variable orifice valves, the pressure limiting valve of the present invention minimizes the exhalation resistance due to its spring and disc design.

It will be understood by those skilled in the art that many variations and modifications may be made in the present invention without departing from the spirit and the scope thereof.

What is claimed is:

1. An improved adjustable pressure limiting valve, comprising:

a valve body including a first generally cylindrical member provided with a generally cylindrically formed passageway extending therethrough and having opposed first and second open ends, said first end for receiving pressurized gas from a first source and said second end for receiving pressurized gas from a second source, said valve body further including a second generally cylindrical member intermediate said opposed ends and generally perpendicular to said first generally cylindrical member, said second member provided with a generally centrally formed second passageway extending therethrough and in fluid communication with said first passageway through a circular inlet opening formed in said second member, said second generally cylindrical member including a generally annular valve seat provided in said second passageway and generally surrounding said circular inlet opening, and the exterior of said second generally cylindrical member provided with a plurality of axially aligned and spaced apart spiral grooves, said grooves having a common angle of inclination;

a generally circular disc residing in said second passageway and for being exposed through said inlet opening to pressurized gas present in said first passageway, said disc for being forced into engagement with said valve seat to cover said inlet opening to substantially prevent pressurized gas present in said first passageway to vent through said inlet opening, and said disc provided with a generally cylindrically formed bleed hole extending transversely therethrough for constantly placing said first passageway in fluid communication with said second passageway;

a generally cylindrical cap including a circular top and a downwardly extending cylindrical wall circumscribing said top and oriented generally perpendicularly with respect therethrough, a plurality of inwardly extending groove engaging tabs provided on the interior of said wall, and said tabs provided with substantially the same angle of inclination as said spiral grooves and said tabs spaced substantially equally circumferentially with respect to each other around said interior of said wall, each of said groove engaging tabs residing in one of said spiral grooves to mount said cap rotatably with respect to said second generally cylindrical member and for rotation with respect thereto in both the clockwise and counterclockwise directions of rotation, said top provided with a generally cylindrically formed vent port in fluid communication with the atmosphere and said second passageway and said vent port and said bleed hole formed in said disc for constantly venting pressurized gas present in said first passageway to the atmosphere to establish a base line pressure for said pressurized gas present in said first passageway;

a spring residing in said second passageway intermediate and in engagement with said disc and the underside of said top of said cap, said spring for applying a first force to said disc to force said disc into engagement with said valve seat, upon rotation of said cap in one of said directions of rotation said spring being increasingly compressed by said cap to cause said spring to gradually increase said first force and upon rotation of said cap in the other direction of rotation said cap allowing said spring to increasingly decompress to cause said spring to gradually decrease said first force; and upon pressurized gas in said first passageway producing a second force acting on said disc in opposition to and in excess of said first force said disc being moved out of engagement with said valve seat to permit at least a portion of said pressurized gas present in said first passageway to be exhausted through said inlet opening, said second passageway and said vent port thereby providing said pressurized gas present in said first passageway with a peak pressure substantially equal to the pressure of said pressurized gas producing said second force in excess of said first force.

* * * * *